United States Patent [19]

Grollier et al.

[11] Patent Number: 4,931,066
[45] Date of Patent: Jun. 5, 1990

[54] DYEING COMPOSITION FOR KERATINOUS FIBRES CONTAINING AT LEAST ONE CO-SOLUBILIZED N-SUBSTITUTED 2-NITRO-PARA-PHENYLENEDIAMINE AND PROCESS FOR DYEING KERATINOUS FIBRES THEREWITH

[75] Inventors: Jean-Francois Grollier, Paris; Jean Cotteret, Franconville; Georges Rosembaum, Asnieres, all of France

[73] Assignee: L'Oreal, Paris, France

[21] Appl. No.: 764,074

[22] Filed: Aug. 9, 1985

[30] Foreign Application Priority Data

Aug. 13, 1984 [LU] Luxembourg ............................ 85501

[51] Int. Cl.$^5$ ............................................... A61K 7/13
[52] U.S. Cl. ............................................ 8/410; 8/405; 8/407; 8/408; 8/415; 8/426; 8/428; 8/435
[58] Field of Search .................. 8/405, 407, 408, 410, 8/415, 426, 428, 435

[56] References Cited

U.S. PATENT DOCUMENTS 3,168,442  2/1965  Brunner et al. ........................ 8/415

FOREIGN PATENT DOCUMENTS 2112818  7/1983  United Kingdom ................... 8/410

OTHER PUBLICATIONS

Chemical Abstracts, 93:241175m, (1980).
Chemical Abstracts, 88:105417m, (1977).

*Primary Examiner*—Douglas W. Robinson
*Attorney, Agent, or Firm*—Cushman, Darby & Cushman

[57] ABSTRACT

The invention relates to a dyeing composition for keratinous fibres containing, in a suitable vehicle, at least one 2-nitro-para-phenylenediamine direct dye, in free or salified form and also at least one xanthine derivative of formula (II)

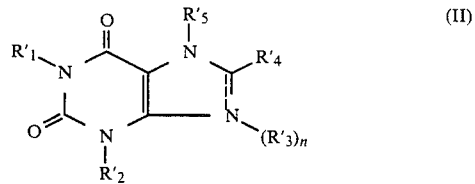

where $n=0$ or $1$, $R'_3=H$, $R'_1$, $R'_2$, $R'_4$ and $R'_5$ are substituents having various significances, the said compound of formula (II) being in free or salified form. They can be used for dyeing hair.

20 Claims, No Drawings

DYEING COMPOSITION FOR KERATINOUS FIBRES CONTAINING AT LEAST ONE CO-SOLUBILIZED N-SUBSTITUTED 2-NITRO-PARA-PHENYLENEDIAMINE AND PROCESS FOR DYEING KERATINOUS FIBRES THEREWITH

The present invention relates to a dyeing composition for keratinuous fibres, and especially for living human hair, containing at least one nitrated direct dye of the N-substituted 2-nitro-para-phenylenediamine series. The invention also relates to a dyeing process using the said compositions.

It is known to use nitro-para-phenylenediamines and their substitution products in the composition of dyeing solutions for dyeing keratinous fibres.

These dyes endow the hair with a direct coloration also known as semi-permanent, and they can also be used in oxidation dyeing compositions to obtain, with the oxidation dyes, complementary highlights and shades rich in highlights.

In hair dyeing, blue, red, mauve and violet tints are necessary as components for achieving the desired tints, and the use has already been proposed, as direct hair dyes of this type, of 2-nitro-para-phenylenediamine derivatives in which the amino group in the 4 position is mono- or disubstituted, while the amino group in the 1 position can, for its part, be monosubstituted and the aromatic ring can be either substituted or unsubstituted in the remaining positions.

These classical 2-nitro-para-phenylenediamine derivatives are more often than not insufficiently soluble or dispersible in water, and this constitutes a major disadvantage in hair dyeing for achieving dark shades; if the dye is not solubilized in the dyeing medium, irregularities in dyeing result, with a great risk of obtaining weaker coloring than that envisaged. In fact, in the particular case of dyeing formulations rich in dyes for obtaining varied shades, or in the case of poor solubilizing media, the dyes can recrystallize, remain in the dye bath and, as a result, do not pass onto the hair.

Dyeing preparations produced from 2-nitro-para-phenylenediamine derivatives in which the amino group in the 4 position is mono- or disubstituted and in which the amino group in the 1 position can optionally be monosubstituted, the aromatic ring being substituted or unsubstituted in the remaining positions, have consequently not hitherto completely satisfied the demands of good dyeing.

Quite surprisingly, we have discovered, according to the present invention, that, by introducing a specified xanthine derivative into a dyeing composition containing at least one red, mauve, blue or violet nitrated direct dye which is a 2-nitro-para-phenylenediamine in which the amino group in the 4 position is mono- or disubstituted with lower alkyl or hydroxyalkyl radicals and in which the amino group in the 1 position is optionally monosubstituted by a lower alkyl or hydroxyalkyl radical, the aromatic ring being substituted or unsubstituted on the para position to the $NO_2$, the solubility of the red, mauve, blue or violet nitrated direct dye or dyes is improved by the phenomenon of co-solubilization.

The dyeing compositions according to the invention can thus make better use of the potential dyeing capacity of the substituted 2-nitro-para-phenylenediamine direct dyes as mentioned above.

In effect, the co-solubilization agent introduced makes it possible to reduce or avoid the risks of recrystallization of the 2-nitro-para-phenylenediamine direct dyes in dyeing formulations rich in these dyes or in dyeing formulations having a poor solubilizing medium. The co-solubilization agent used in the composition according to the invention also has the advantage of being colorless, and consequently of not modifying in any way the shades, which may result from the combination of several dyes of different colors, initially desired.

The present invention accordingly provides a dyeing composition for keratinous fibres, and more especially for human hair, containing, in a suitable vehicle, at least one 2-nitro-para-phenylenediamine direct dye, of formula (I):

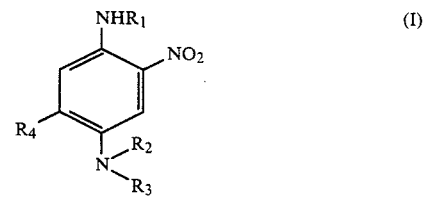

in which formula:
  $R_1$ denotes hydrogen, a lower alkyl radical having 1 or 2 carbon atoms or a $\beta$-hydroxyethyl radical;
  $R_2$ denotes a $\beta$-hydroxyethyl radical;
  $R_3$ denotes hydrogen, a lower alkyl radical having 1 or 2 carbon atoms or a $\beta$-hydroxyethyl radical;
  $R_4$ denotes hydrogen, a lower alkyl radical having from 1 to 4 carbon atoms or a halogen group, with the proviso that, when $R_4$ is other than hydrogen, $R_3$ denotes hydrogen; in free or salified form; and also at least one xanthine derivative corresponding to the following formula (II):

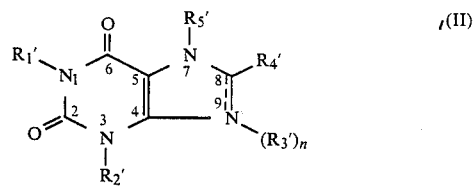

in which formula:
  $n=0$ or 1 such that when $n=0$, represents a double bond and when $n=1$, represents a single bond;
  $R_1'$ and $R_2'$ denote a hydrogen atom, a lower alkyl group having from one to four carbon atoms or a lower hydroxyalkyl group having two or three carbon atoms;
  $R_3'$ denotes a hydrogen atom;
  $R_4'$ denotes a hydrogen atom, a lower alkyl group having from one to four carbon atoms, a lower alkoxy group having from one to four carbon atoms or a halogen, $R_4'$ being able, in addition, to denote an oxo group (i.e. $CHR_4'$, becomes $C=O$) when $R_1'=R_2'=R_5'=H$ and $n=1$;
  $R_5'$ denotes a hydrogen atom, a lower alkyl group having from one to four carbon atoms, a lowr mono- or polyhydroxyalkyl group, a 3-(2-hydroxyethyl)(methyl)-amino-2-hydroxypropyl chain; a lower alkyl group having from one to four carbon atoms, substituted with a heterocyclic system containing two identical hetero atoms such as nitrogen or two different hetero atoms such as nitrogen and oxygen, and more especially a 1-piperidinoethyl, 1-piperazinoethyl, 4-morpholinomethyl, 4-morpholinoethyl group; an acetic group or a 3-propane-sulphonic group; - such that $R_1'$, $R_2'$, $R_3'$, $R_4'$ and $R_5'$ do not all denote hydrogen simultaneously; the compounds of formula (II) being present either in free form or in a form salified by inorganic or organic acids.

The compounds of formula (II) which are advantageously chose for the dyeing compositions according to the invention are theophylline, caffeine, 7-(2,3-dihydroxypropyl)theophylline and uric acid.

Among the compounds of formula (I), the solubility of which can be increased as a result of the presence of the compound of formula (II), the following may be mentioned in particular:

(a) the compound of which $R_1$=methyl, $R_2$=$R_3$=β-hydroxyethyl and $R_4$=H;

(b) the compound for which $R_1$=$R_3$=methyl, $R_2$=β-hydroxyethyl and $R_4$=H;

(c) the compound for which $R_1$=$R_2$=$R_3$=β-hydroxyethyl and $R_4$=H;

(d) the compound for which $R_1$=$R_3$=H, $R_2$=β-hydroxyethyl and $R_4$=methyl; as well as the corresponding salts of acids.

By way of explanation, the solubility limits at 18° C. of a dye of formula (I) in the presence of a fixed amount of several compounds of formula (II) have been collated in the following table, these solubility limits being measured in the following composition:

| Compound of formula (II) | y g |
| Compound of formula (I) | x g |
| Ethylene glycol monoethyl ether | 10 g |
| 2-Amino-2-methyl-1-propanol qs | pH 9.6 |
| Water qs | 100 g | x is the maximum amount of the dye in question of formula (I) which can be dissolved in the particular medium thus defined.

To determine the solubilities, the procedure is as follows: a large excess of dye of formula (I) is dispersed with y g of compound of formula (II) in the cosmetic base described above. The composition is left for 15 minutes at 60° C. (water bath) and then cooled with the ambient air with stirring for 30 minutes (checking that the ambient temperature is greater than 18° C.). After these 30 minutes, the composition is introduced into a chamber maintained at 18° C. The composition must remain there for at least 48 hours. After its removal from the chamber, the composition is immediately filtered. The collected filtrates are then analysed by high performance liquid chromatography (HPLC) to determine the dye content.

| Dye of formula (I) | Solubility limits of the dye of formula (I) | | | |
| --- | --- | --- | --- | --- |
| | Alone y = 0 | Combined with the compound of formula (II) y = 1.5 g | | |
| | | caffeine | theophylline | 7-(2,3-dihydroxypropyl)theophylline |
| 1-(β-hydroxyethyl)amino-2-nitro-4-[bis(β-hydroxyethyl)amino]benzene | 0.74% | 1.90% (2.57)* | 1.69% (2.28)* | 1.45% (1.96)* |
| 1-amino-2-nitro-4-(β-hydroxyethyl)amino-5-methylbenzene | 0.07% | 0.41% (5.86)* | 0.19% (2.71)* | 0.24% (3.43)* |

*The figure given in brackets shows the improvement in solubility of the dye of formula (I) in the presence of the compound of formula (II). Thus, the dye of formula (I), 1-(β-hydroxyethyl) amino-2-nitro-4-[bis(β-hydroxyethyl)amino]benzene, is 2.57 times more soluble in the aforementioned medium when the amount of caffiene in the said medium increases from 0 to 1.5 g.

The compounds of formula (I) are, in particular, described in French Patent Nos. 1,101,904, 1,411,124, 1,454,313 and 1,454,314, as well as in U.S. Pat. No. 3,168,422 and in French Patent Application No. 81/19,393.

The compounds of formula (II) are well known.

According to preferred embodiments, the compound or compounds of formula (I) (and/or the corresponding salts) is/are present in the dyeing composition according to the present invention at a concentration of 0.05% to 5% by weight, and especially from 0.1 to 3% by weight, expressed as free base, relative to the total weight of the composition; the compound or compounds of formula (II) (and/or the corresponding salts) is/are present in the composition at a concentration of from 0.1% to 5% by weight, and preferably from 0.3% to 3% weight, expressed as free base, relative to the total weight of the composition.

The dyeing compositions according to the invention can contain, in addition to the compounds of formulae (I) and (II), in free or salified form, one or more of the following, for example:
(1) oxidation bases such as para-phenylenediamines, para-aminophenols and heterocyclic bases;
(2) couplers such as meta-phenylenediamines, meta-aminophenols or metadiphenols, or heterocyclic couplers, when the composition contains at least one oxidation base;
(3) ortho-phenylenediamines and ortho-aminophenols, optionally containing substituents on the ring or on the amino groups, or alternatively ortho-diphenol;
(4) dye precursors of the benzene series, containing on the ring at least three substituents chose from the group consisting of hydroxy, methoxy or amino groups;
(5) dye precursors of the naphthalene series;
(6) leuco derivatives of indoanilines, indophenols or indoamines;
(7) nitrated direct dyes different from those of formula (I);
(8) non-nitrated direct dyes such as azo dyes or anthraquinone dyes.

The dyeing compositions according to the invention can contain, as a suitable vehicle, water and/or organic solvents which are acceptable from the cosmetic standpoint and, more especially, alcohols such as ethyl alcohol, isopropyl alcohol, benzyl alcohol and phenylethyl alcohol, or glycols or glycol ethers such as, ethylene glycol and its monomethyl, monoethyl and monobutyl ethers, propylene glycol, butylene glycol and dipropylene glycol, as well as alkyl ethers of diethylene glycol, such as diethylene glycol monoethyl ether and monobutyl ether, typically at concentrations from 0.5 to 20%, and preferably from 2 to 10%, by weight relative to the total weight of the composition.

There can also be incorporated in the composition according to the invention fatty amides, such as the mono- and diethanolamides of acids derived from copra, lauric acid or oleic acid, typically at concentrations of 0.05 to 10% by weight.

Anionic, cationic, nonionic or amphoteric surfactants, or mixtures thereof, can also be incorporated in the composition according to the invention. The surfactants are preferably present in the composition according to the invention in a proportion from 0.1 to 50% by weight, and advantageously from 1 to 20% by weight, relative to the total weight of the composition.

Among surfactants, there may be mentioned more especially anionic surfactants used alone or in combination, such as alkali metal salts, magnesium salts, ammonium salts, amine salts or alkanolamine salts of the following compounds: ½ alkyl sulphates, alkyl ether sulphates, ethoxylated or non-ethoxylated alkylamide sulphates, alkyl sulphonates, alkylamide sulphonates, alpha-olefin sulphonates; • alkyl sulphoacetates; the alkyl radicals of these compounds having a linear chain of 12 to 18 carbon atoms.

It is also possible to use, in the form of salts mentioned above, fatty acids such as lauric, myristic, oleic, ricinoleic, palmitic or stearic acids, coconut oil or hydrogenated coconut oil acids, or carboxylic acids of polyglycol ethers.

By way of cationic surfactants, there may be mentioned more especially fatty amine salts, quaternary ammonium salts such as alkyldimethylbenzylammonium, alkyltrimethylammonium, alkyldimethylhydroxyethylammonium and dimethyldialkylammonium chlorides and bromides, alkylpyridinium salts and imidazoline derivatives. The alkyl groups of the abovementioned quaternary ammonium derivatives are long-chain groups preferably having 12 to 18 carbon atoms.

There may also be mentioned amine oxides, these compounds having a cationic nature.

Among amphoteric surfactants which can be used, there may be mentioned in particular alkylaminomono- and -dipropionates, betaines such as alkylbetaines, N-alkylsulphobetaines and N-alkylaminobetaines, the alkyl radical having 1 to 22 carbon atoms, and cycloimidinium compounds such as alkylimidazolines.

Among nonionic surfactants which can optionally be used in the compositions according to the invention, there may be mentioned condensation products of a mono- alcohol, alkylphenol, amide or α-diol with glycidol, such as the compounds prepared according to French Patents 2,091,516, 2,169,787 and 2,328,763; the compounds of formula:

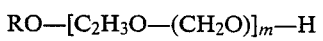

in which R denotes an alkyl, alkenyl or alkylaryl radical having 8 to 22 carbon atoms, m being an integer from 1 to 10; polyethoxylated or polyglycerolated alcohols, alkylphenols or fatty acids having a $C_8$ to $C_{18}$ linear fatty chain; condensates of ethylene oxide and propylene oxide with fatty alcohols; polyethoxylated fatty amides containing at least 5 moles of ethylene oxide; and polyethoxylated fatty amines.

The thickening products which can be added to the composition according to the invention are advantageously sodium alginate, gum arabic, guar gum, cellulose derivatives such as methylcellulose, hydroxyethylcellulose, hydroxypropylmethylcellulose, the sodium salt of carboxymethylcellulose and acrylic acid polymers; inorganic thickening agents such as bentonite can also be used.

These thickeners can be used along or in combination, and are preferably present in a proportion from 0.5 to 5%, advantageously from 0.5 to 3%, by weight relative to the total weight of the composition.

Thde dyeing compositions according to the invention can be formulated at acid, neutral or alkaline pH; the pH can generally vary from 4 to 10.5, and preferably from 6 to 10. Among the alkalization agents which can be used, there may be mentioned alkanolamines and alkali metal or ammonium hydroxides and carbonates. Among acidification agents which can be used, there may be mentioned lactic acid, acetic acid, tartaric acid, phosphoric acid, hydrochloric acid and citric acid.

The dyeing compositions can contain, in addition, various conventional adjuvants such as antioxidants, perfumes, sequestering agents, film-forming products and treatment agents, dispersants, hair conditioning agents, preservatives and opacifiers, as well as any other adjuvants customarily used in cosmetics.

The dyeing composition according to the invention can take various conventional forms, for hair dyeing, such as thickened or gelified liquids, creams or aerosol foams, or any other form suitable for carrying out dyeing of keratinous fibres.

When it contains at least one oxidation base, the dyeing composition according to the invention can be mixed, at the time of use, with an oxidizing agent such as a peroxide or alkali metal persalt such as hydrogen peroxide, sodium peroxide, potassium peroxide, sodium perborate, sodium percarbonate and urea peroxide.

The present invention also provides a new process for dyeing keratinous fibres, and especially human hair, characterized in that the dyeing composition of this invention is left to act on dry or damp keratinous fibres. The compositions according to the invention can be used as non-rinsed lotions when the compositions do not contain an oxidation dye, that is to say the compositions according to the invention are applied to the keratinous fibres and these are then dried without intermediate rinsing. In the other modes of use, the dyeing compositions according to the invention are applied to the keratinous fibres for, say, 3 to 60 minutes, preferably 5 to 45 minutes, and these are then rinsed, optionally washed, rinsed again and dried.

The dyeing compositions according to the invention can be applied to natural or dyed hair which has been permanently waved or otherwise, or to strongly or lightly bleached hair, optionally permanently waved.

The following Examples further illustrate the present invention.

EXAMPLE 1
The following composition is prepared:

| | |
|---|---|
| 1-(β-Hydroxyethyl)amino-2-nitro-4-[bis(β-hydroxyethyl)amino]benzene | 1.8 g |
| 1-(β-Hydroxyethyl)amino-2-nitro-4-[(β-hydroxyethyl)amino]benzene | 0.1 g |
| 2-Methoxy-1-(β-hydroxyethyl)amino-4-nitrobenzene | 0.1 g |
| (3-Methylamino-4-nitrophenoxy)ethanol | 0.1 g |
| 1-Amino-2-nitro-4-[(β-hydroxyethyl)amino]benzene | 0.3 g |
| 3-Methylamino-4-nitrophenyl β,γ-dihydroxypropyl ether | 0.6 g |
| Caffeine | 1.6 g |
| Lauric diethanolamide | 2.5 g |
| Lauric acid | 1.5 g |
| Lauric alcohol treated with 40 mols of ethylene oxide | 3.0 g |
| 2-Ethoxyethanol | 5.0 g |
| Hydroxyethylcellulose sold by HERCULES under the name "Natrosol 250 HHR" | 0.1 g |
| 2-Amino-2-methyl-1-propanol qs pH | 9.5 |
| Demineralized water qs | 100 g |

This composition is applied for 30 minutes on chestnut-colored hair.

After the hair has been rinsed and dried, a purple-violet brown coloration is obtained.

EXAMPLE 2
The following composition is prepared:

| | |
|---|---|
| 1-Methylamino-2-nitro-4-[methyl(β-hydroxyethyl)amino]benzene | 0.3 g |
| 2-Amino-4-methyl-5-(β-hydroxyethyl)amino-1-nitrobenzene | 0.2 g |
| [4-(β-Hydroxyethyl)amino-3-nitrophenoxy]ethanol | 1.0 g |
| 7-(2,3-Dihydroxypropyl)theophylline | 0.9 g |
| Nonylphenol treated with 9 mols of ethylene oxide | 8.0 g |
| Oleic diethanolamide | 2.0 g |
| 2-Butoxyethanol | 10.0 g |
| Hydroxypropylcellulose sold by HERCULES under the name "KLUCEL G" | 0.15 g |
| 2-Amino-2-methyl-1-propanol qs pH | 9.0 |
| Demineralized water qs | 100 g |

This composition is applied for 20 minutes on light chestnut-colored hair.

The hair is rinsed and dried; a coppery red coloration is obtained.

EXAMPLE 3
The following composition is prepared:

| | |
|---|---|
| 1,4-Diaminobenzene | 0.2 g |
| 1-Amino-4-hydroxybenzene | 0.1 g |
| 1-Amino-4-methyl-3-hydroxybenzene | 0.05 g |
| 2-Amino-4-methyl-5-(β-hydroxyethyl)amino-1-nitrobenzene | 0.25 g |
| 7-(2,3-Dihydroxypropyl)theophylline | 1.5 g |
| Cetyl and stearyl alcohols in a 50:50 mixture | 18.0 g |
| 2-Octyldodecanol | 3.0 g |
| Cetyl/stearyl alcohol treated with 15 moles of ethylene oxide | 3.0 g |
| Ammonium lauryl sulphate | 12.0 g |
| Sodium bisulphite (35° Be) | 2.0 g |
| Ammonia solution (22° Be) | 10.0 g |
| Demineralized water qs | 100 g |

This cream is diluted at the time of use with 1.5 times its weight of an oxidizing milk containing "20 volumes" hydrogen peroxide. After the mixing, the new cream obtained is applied for 30 minutes on light chestnut-colored hair.

After the hair has been rinsed, followed by shapooing, it is dried; an auburn dark blonde coloration is obtained.

EXAMPLE 4
The following composition is prepared:

| | |
|---|---|
| 2-Amino-4-chloro-5-(β-hydroxyethyl)amino-1-nitrobenzene | 0.6 g |
| 4-(β-Hydroxyethyl)amino-3-nitrophenyl β,γ-dihydroxypropyl ether | 0.4 g |
| 1-Methylamino-2-nitro-4-[bis(β-hydroxyethyl)amino]benzene | 0.15 g |
| 1-(β-Methoxyethyl)amino-4-aminobenzene dihydrochloride | 0.4 g |
| (2,4 Diaminophenoxy)ethanol dihydrochloride | 0.05 g |
| 1,4-Dihydroxybenzene | 0.15 g |
| 1-Amino-3-hydroxybenzene | 0.1 g |
| 1,3-Dihydroxybenzene | 0.25 g |
| Theophylline | 1.6 g |
| Oleic alcohol glycerolated with 2 moles of glycerol | 5.0 g |
| Oleic alcohol glycerolated with 4 moles of glycerol | 5.0 g |
| Oleic acid | 5.0 g |
| Oleic diethanolamide | 12.0 g |
| Oleic diethanolamine | 5.0 g |
| Ethanol | 10.0 g |
| 2-Ethoxyethanol | 12.0 g |
| Ethylenediaminetetraacetic acid | 0.2 g |
| Ammonia solution (22° Be) | 10.2 g |
| Sodium bisulphite (35° Be) | 1.3 g |
| Demineralized water qs | 100 g |

This liquid is diluted at the time of use with an equal weight of "20 volumes" hydrogen peroxide. The gel obtained is applied for 30 minutes on chestnut-colored hair. The shade obtained after rinsing, shapooing and drying is a purple-violet light chestnut.

EXAMPLE 5
The following composition is prepared:

| | |
|---|---|
| 1-Methylamino-2-nitro-4-[bis(β-hydroxyethyl)amino]benzene | 1.1 g |
| 1-(β-Hydroxyethyl)amino-2-nitro-4-[methyl-(β-hydroxyethyl)amino]benzene | 0.1 g |
| 3-Methylamino-4-nitrophenyl β,γ-dihydroxypropyl ether | 0.6 g |
| 2-Amino-4-methyl-5-(β-hydroxyethyl)amino-1-nitrobenzene | 0.05 g |
| Theophylline | 1.5 g |
| Nonylphenol treated with 9 mols of ethylene | 8.0 g |

-continued

EXAMPLE 5
The following composition is prepared:

| | |
|---|---|
| oxide | |
| Lauric diethanolamide | 2.0 g |
| 2-Butoxyethanol | 10.0 g |
| Hydroxypropylcellulose sold under the name "KLUCEL G" by HERCULES | 0.15 g |
| Monoethanolamine qs pH | 9.5 |
| Demineralized water qs | 100 g |

This liquid is applied on chestnut-colored hair for 20 minutes; the hair is rinsed and dried; an ashen chestnut coloration is obtained.

We claim:

1. A hair dye composition for living human hair comprising a solution in water, as a cosmetically acceptable vehicle, of
   (1) a direct dye selected from the group consisting of
      (a) a direct dye having the formula

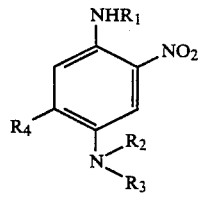

wherein
   $R_1$ represents hydrogen, methyl, ethyl or β-hydroxyethyl,
   $R_2$ represents β-hydroxyethyl,
   $R_3$ represents hydrogen, methyl, ethyl or β-hydroxyethyl and
   $R_4$ represents hydrogen, halogen or alkyl having 1-4 carbon atoms, with the proviso that when $R_4$ is other than hydrogen, $R_3$ represents hydrogen, and
   (b) a salt of the direct dye defined in (a) said direct dye being present in an amount ranging from 0.05 to 5 percent by weight, expressed as free base, based on the total weight of said composition, and
   (2) a co-solubilizing amount of a xanthine derivative selected from the group consisting of
      (a') a xanthine derivative of the formula

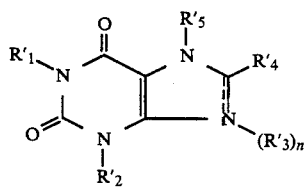

wherein
   n=0 or 1.such that when n=0, represents a double bond and when n=1, represents a single bond,
   $R_1'$ and $R_2'$ independently represent hydrogen, alkyl having 1-4 carbon atoms or hydroxyalkyl wherein the alkyl moiety has 2-3 carbon atoms,
   $R_3'$ represents hydrogen,
   $R_4'$ represents hydrogen, halogen, alkyl having 1-4 carbon atoms, alkoxy having 1-4 carbon atoms or an oxo group when $R_1'=R_2'=R_5'=H$ and n=1; and
   $R_5'$ represents hydrogen, alkyl having 1-4 carbon atoms, lower mono- or polyhydroxyalkyl, 3-(2-hydroxyethyl) (methyl)amino-2-hydroxypropyl chain, alkyl having 1-4 carbon atoms and substituted by a heterocycle selected from the group consisting of 1-piperidinoethyl, 1-piperazinoethyl, 4-morpholinomethyl and 4-morpholinoethyl; an acetic or 3-propane sulfonic group; with the proviso that $R_1'$, $R_2'$, $R_3'$, $R_4'$ and $R_5'$ are not all hydrogen simultaneously; and
   (b') an inorganic or organic acid salt of the xanthine derivative defined in (a')
      said xanthine derivative being present in an amount ranging from 0.1 to 5 percent by weight, expressed as free base, based on the total weight of said composition.

2. The hair dye composition of claim 1 wherein said cosmetically acceptable vehicle also includes an organic solvent, said solvent being present in an amount ranging from 0.5 to 20 weight precent based on the total weight of said composition.

3. The hair dye composition of claim 2 wherein said organic solvent is ethyl alcohol, isopropyl alcohol, benzyl alcohol, phenylethyl alcohol, ethylene glycol, the monomethyl, monoethyl or monobutyl ether of ethylene glycol, propylene glycol, butylene glycol, dipropylene glycol, diethylene glycol monoethyl ether or diethylene glycol monobutyl ether.

4. The hair dyeing composition of claim 1 wherein said xanthine derivative is selected from the group consisting of theophylline, caffeine, 7-(2,3-dihydroxy propyl) theophylline and uric acid.

5. The hair dye composition of claim 1 where in the direct dye of formula I, $R_1$=methyl, $R_2=R_3=$β-hydroxyethyl and $R_4$=H.

6. The hair dye composition of claim 1 where in the direct dye of formula I, $R_1=R_3$=methyl, $R_2=$β-hydroxyethyl and $R_4$=hydrogen.

7. The hair dye composition of claim 1 where in the direct dye of formula I, $R_1=R_2=R_3=$β-hydroxyethyl and $R_4$=hydrogen.

8. The hair dye composition of claim 1 where in the direct dye of formula I, $R_1=R_3$=hydrogen, $R_2=$β-hydroxyethyl and $R_4$=methyl.

9. The hair dye composition of claim 1 wherein said direct dye is present in an amount ranging from 0.1 to 3 percent by weight based on the total weight of said composition.

10. The hair dye composition of claim 1 wherein said xanthine derivative is present in an amount ranging from 0.3 to 3 percent by weight based on the total weight of said composition.

11. The hair dye composition of claim 2 wherein said cosmetically acceptable vehicle is present in an amount ranging from 2 to 10 weight percent based on the total weight of said composition.

12. The hair dye composition of claim 1 which also includes a mono- or diethanolamide of an acid derived from copra, lauric acid or oleic acid, present in an amount ranging from 0.05 to 10 weight percent based on the total weight of said composition.

13. The hair dye composition of claim 1 which also contains a surfactant present in an amount ranging from 0.1 to 50 weight percent based on the total weight of said composition.

14. The hair dye composition of claim 1 which also contains a thickening agent present in an amount ranging from 0.5 to 5 weight percent based on the total weight of said composition.

15. The hair dye composition of claim 14 wherein said thickening agent is present in an amount ranging from 0.5 to 3 weight percent based on the total weight of said composition.

16. The hair dye composition of claim 1 having a pH ranging from 4 to 10.5.

17. The hair dye composition of claim 1 having a pH ranging from 6 to 10.

18. A process for dyeing living human hair comprising applying to the hair a hair dyeing amount of the hair dye composition of claim 1, permitting said hair dye composition to remain in contact with the hair for a period of time ranging from 3 to 60 minutes, rinsing the hair and drying the hair.

19. The process of claim 18 wherein subsequent to rinsing the hair and prior to drying the hair, the hair is washed and rinsed.

20. A process for dyeing living human hair comprising applying to the hair a hair dyeing amount of the hair dye composition of claim 1, permitting said hair dye composition to remain in contact with the hair for a period of time ranging from 3 to 60 minutes and drying the hair without an intermediate rinse thereof.

* * * * *